United States Patent [19]

Jolles et al.

[11] 4,014,992

[45] Mar. 29, 1977

[54] ACETYLATED WATERSOLUBLE EXTRACTS OF CORYNEBACTERIA, PROCESS FOR OBTAINING THEM AND THEIR USE

[75] Inventors: Pierre Jolles, Paris; Daniele Migliore-Samour, Kremlin-Bicetre (Val de Marne), both of France

[73] Assignee: Agence Nationale de Valorisation de la Recherche (ANVAR), Neuilly-sur-Seine, France

[22] Filed: Apr. 30, 1975

[21] Appl. No.: 573,199

[30] Foreign Application Priority Data

May 6, 1974  France .............................. 74.15571

[52] U.S. Cl. .................................. 424/92; 424/88; 424/95; 424/123; 424/177; 424/195
[51] Int. Cl.² .................. A61K 39/02; A61K 39/00
[58] Field of Search ............. 424/88, 95, 123, 177, 424/195, 92

[56] References Cited

FOREIGN PATENTS OR APPLICATIONS 2,189,021  1/1974  France
2,331,144  1/1974  Germany

OTHER PUBLICATIONS

Chemical Abstracts, vol. 80:144339s & 144340k.
Chemical Abstracts, vol. 79:30413k.

*Primary Examiner*—Donald B. Moyer
*Attorney, Agent, or Firm*—Burgess, Dinklage & Sprung

[57] ABSTRACT

There is disclosed a process for obtaining acetylated watersoluble extracts of corynebacteria and specifically of *Corynebacterium parvum*, of low molecular weight. Said process comprises acetylating delipidated bacterial residues of bacteria cells and isolating the watersoluble extracts by physico-chemical means. Said extracts are useful as immunological adjuvants in veterinary and human therapy.

7 Claims, No Drawings

ACETYLATED WATERSOLUBLE EXTRACTS OF CORYNEBACTERIA, PROCESS FOR OBTAINING THEM AND THEIR USE

This invention relates to a process for obtaining acetylated watersoluble extracts of low molecular weight derived from cells of corynebacteria, the watersoluble extracts thus obtained and pharmaceutical compositions containing the same. The invention has also for its object the use of such watersoluble extracts as immunological adjuvants.

In accordance with the invention, watersoluble extracts contain diaminopimelic acid and have a molecular weight between 1000 ± 200 and 8000 ± 200.

The process of the invention comprises the steps of subjecting to acetylation delipidated bacterial residues of corynebacteria cells and of isolating the watersoluble extracts by conventional physico-chemical means; the thus-obtained watersoluble extracts are advantageously purified by conventional physico-chemical means.

The acetylation is generally effected in a mixture of acetic anhydride and pyridine, containing preferably 2 volumes acetic anhydride for 3 volumes pyridine at a temperature of about 20° to 35° C. The reaction is completed after stirring during a period of about 50 to 75 hours.

In the meaning of the present specification, the corynebacteria used in the process of the invention are corynebacteria containing diaminopimelic acid (DAP). Certain corynebacteria answering to this general definition contain meso-DAP and arabinogalactan. They are known as optionally anaerobic. An example of such corynebacteria is *C. diphteriae*.

Other corynebacteria in conformity with this definition and suitable herein include LL DAP and no arabinogalactan. They are known as strictly anaerobic. Amongst corynebacteria of this latter type there can be mentioned for example *C. acnes*, *C. parvum*, *C. anaerobium* and *C. granulosum* and the like.

As a relevant bibliographic reference, one may cite the article by Karl Heinz SCHLEIFER and Otto KANDLER, in Bacteriological Reviews Vol. 36 No. 4, Dec. 1972 pages 407–477, where they are included an enumeration of corynebacteria and the properties thereof. The disclosures of said article are included as a reference in the present specification.

Corynebacteria cells, which are particularly preferred for carrying out the invention, are *Corynebacterium parvum*.

The corynebacteria cells used in the process of the invention are previously subjected to delipidation by using e.g. the method disclosed by A. Aebi et al [Bull. Soc. Chim. Biol., 35, 661 (1953)].

Watersoluble extracts are thereafter isolated by alcohol extraction followed by a water extraction.

In accordance with a preferred embodiment of the invention, watersoluble extracts are isolated as follows:
 by treatment of the reaction medium obtained after acetylation by means of an alcohol such as ethanol,
 by separation of insoluble material by centrifuging;
 by concentration of the alcoholic solution;
 by treatment of the thus-obtained residue with distilled water;
 by separation of the water-insoluble fraction by centrifuging; and
 by lyophilization, i.e. freeze-drying, of supernatant aqueous layer which contains acetylated watersoluble extracts which are accordingly soluble both in a pyridine-alcohol mixture and in water.

In the present process the about 10:1 (by volume) ethanol-pyridine mixture may advantageously be used as pyridine-alcohol mixture; all centrifuging steps are advantageously effected at a low temperature, preferably a temperature of about 0° to 6° C.

According to a particularly preferred embodiment of the invention, the watersoluble extracts may be, if desired, purified and separated by suitable physico-chemical methods, including notably chromatography on adsorbents such as DEAE-cellulose, the product known under the trade name "DEAE-Biogel A" or by filtering e.g. on a polyacrylamide gel using for example the products known under the trade names "Biogel P10", "Biogel P6" and "Biogel P4".

The watersoluble extracts, which constitute a further aspect of the invention, consist essentially of a mixture in variable proportions of acetylated watersoluble fragments of the cell wall, optionally in association with acetylated, non aminated reducing sugars. The amount of water soluble fragments of the cell wall contained in watersoluble extracts of the invention varies as a function of specific conditions for carrying out the process of the invention and, in particular, the purification.

Watersoluble fragments of the cell wall consist essentially of disaccharide-tetrapeptide, tetrasaccharide-heptapeptide and the dimer, trimer or tetramer of the last mentioned compound.

The disaccharide-tetrapeptide has the following molecular composition: N-acetylglucosamine (1), N-acetylmuramic acid (1), alanine (2), glutamic acid (1), diaminopimelic acid (1) and its base structure may be represented by the following:

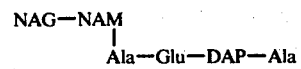

wherein:
 NAG = N-acetylglucosamine
 NAM = N-acetylmuramic acid
 Ala = alanine
 Glu = glutamic acid
 DAP = diaminopimelic acid The tetrasaccharide-heptapeptide has the following molecular composition: N-acetylglucosamine (2), N-acetylmuramic acid (2), alanine (3), glutamic acid (2), diaminopimelic acid (2) and its base structure may be represented as follows:

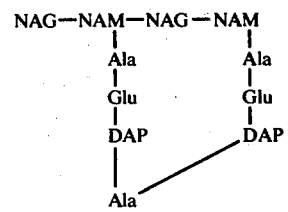

In certain fragments, the free acid or amine function of DAP may be substituted by residues of aspartic acid and glycine which are residues of intercatenary bridgings naturally existing in the cell wall.

Non aminated reducing sugars consist essentially of glucose, mannose and, optionally, galactose.

The structure of thus-obtained watersoluble extracts can be determined by conventional methods of ascertaining aminoacid-, amino-sugar- and non aminated reducing sugar-contents.

By carrying out the purification step previously disclosed, it is possible to obtain according to the invention watersoluble extracts essentially containing-acetylated tetrasaccharide-heptapeptide, optionally in association with acetylated non aminated reducing sugars. Accordingly the raw watersoluble extract provided by the process of the invention yields for example, after filtration on "Biogel P10", followed by chromatography on "DEAE-Biogel A" with elution by suitable solvents, such as diluted acetic acid or a mixture of pyridine and acetic acid, a family of acetylated products comprising acetylated disaccharide-tetrapeptide, acetylated tetrasaccharide-heptapeptide and the dimer, trimer and tetramer of the last mentioned compound, optionally in association with acetylated non aminated reducing sugars. During the filtering and chromatography steps, the watersoluble materials are isolated in the order of successively decreasing molecular weights.

Since the activity of watersoluble extracts of the invention is linked to the presence of diaminopimelic acid, it is especially valuable to isolate, from the raw mixture, products which are present in sufficient amount and which have a high content of diaminopimelic acid. It is accordingly highly interesting to isolate from raw watersoluble extracts, watersoluble extracts containing mainly acetylated tetrasaccharide-heptapeptide, optionally in association with non aminated reducing sugars.

The acetylated watersoluble extracts obtained according to the invention have a valuable activity as immunological adjuvants, in the absence of any arthrogenous activity.

The adjuvant power is determined in the guinea pig, Hartley strain, according to the principle of the method disclosed by R. G. White et al, Immunology, 7 158 (1964), whereas the arthrogenous and protecting powers are ascertained by methods disclosed by F. Bonhomme, C. R. Acad. Sci., serie D, 263, 1422 (1966) and C. R. Acad. Sci., serie D, 265, 2115 (1967).

In the guinea pig, the watersoluble extracts of the invention cause an increase of antibody rate at dosages higher than or equal to 0.1 mg administered intradermally.

The invention has also for its object pharmaceutical compositions containing watersoluble extracts of the invention in association with one or more diluents or adjuvants compatible therewith and, if desired, with other drugs such as antibiotics, decongestive agents and vaccines. In such compositions the concentration of acetylated watersoluble extracts of the invention is generally higher than 0.1%.

Said composition can be administered orally, rectally or parenterally, or even in aerosols.

The dosages are a function of the desired effect and may be comprised between 10 and 50 mg per day for an adult.

The invention will be further illustrated by the following non limiting examples.

EXAMPLE 1

20 g of delipidated bacterial residues obtained from Corynebacterium parvum cells, in accordance with the technique of A. Aebi et al, Bull. Soc. Chim. Biol., 35, 661 (1953), were stirred during 66 hours at 28° C in 500 cm$^3$ of a mixture of acetic anhydride and pyridine (2/3 in volume). Then, there were added 5000 cm$^3$ of ethanol and the mixture was stirred during 5 hours more. The insoluble portion was separated by centrifuging (4000 rpm). The supernatant layer was concentrated to dryness under reduced pressure. The residue was taken up in 100 cm$^3$ of distilled water. The portion insoluble in water was separated by centrifuging (4000 rpm). The supernatant layer was freeze-dried and there was thus-obtained 3.280 g of raw acetylated watersoluble extract.

EXAMPLE 2

The acetylated watersoluble extract obtained in a raw state in example 1 was subjected to purification by filtering on a column of "Biogel P10" (height: 275 cm; diameter 2 cm) with collection of 500 successive fractions of 1.5 cm$^3$ each, the elution being effected by means of 0.1 N acetic acid and being followed by optical reading on a spectrophotometer at 220 and 280 nm.

Fractions No. 293 to 340 were united and freeze-dried. There was thus obtained 0.195 g of a watersoluble extract which was purified by chromatography on "DEAE Biogel A" equilibrated with a 0.01 M solution of pyridine at pH 7.7. When eluting with 0.01 M pyridine, the process yielded 0.110 g of a material rich in diaminopimelic acid whereas, when afterwards eluting with a solvent gradient of 0.01 M to 0.2 M pyridine at pH 7.7 to 5.5, there was obtained 0.080 g of acetylated watersoluble extract having the following characteristics:

aspect: yellowish powder
composition:
a. in aminoacids (molecular ratio): alanine (3), glutamic acid (2), diaminopimelic acid (2); aspartic acid (1) and glycine (1).
b. in aminosugars (molecular ratio): N-acetylglucosamine (2); N-acetylmuramic acid (2).
c. in non aminated reducing sugars: mannose, glucose and traces of galactose.
molecular weight (calculated on the basis of 3 residues of alanine per mole): 3750 ± 250 concentration of aminoacids was 22 ± 3% and concentration of aminosugars was 26 ± 2%, the balance consisting of non aminated reducing sugars and acetyl functions bound by acetylation on the aminated or non aminated reducing sugars, the content of diaminopimelic acid being thus 10 ± 1% by weight.

The watersoluble extract thus-obtained is acetylated tetrasccharide-heptapeptide associated with acetylated non aminated reducing sugars.

We claim:
1. An immunological adjuvant composition comprising low molecular weight acetylated water soluble fragments consisting essentially of a disaccharide-tetrapeptide, a tetrasaccharide-heptapeptide and the dimer, trimer and tetramer of the latter, said adjuvant being produced by the steps of subjecting delipidated bacterial residue of Corynebacterium Parvum containing diaminopimelic acid to acetylation, and extraction with watersoluble alcohol and water, said fragments being acetylated, containing diaminopimelic acid, having a molecular weight between 1000±200 and 8000±200 and being associated with acetylated non-aminated reducing sugars.

2. A composition according to claim 1, wherein acetylation is effected in the presence of pyridine.

3. A composition according to claim 1, wherein the watersoluble extracts are isolated by a watersoluble alcohol extraction of the acetylation product followed by a water extraction of the alcohol extract and freeze-drying of the water extract.

4. A composition according to claim 1, wherein the watersoluble extracts are isolated by processing the acetylation product with ethanol, removal of insolubles, drying of ethanol supernatant which is then treated with distilled water, removal of the fraction insoluble in water and freeze-drying of the supernatant aqueous layer thus obtained.

5. A composition according to claim 1, wherein the process of production includes a purification by chromatography.

6. A composition according to claim 5, wherein chromatography is effected on cellulose.

7. A composition according to claim 1, wherein the process of production includes a filtration on a polyacrylamide gel.

* * * * *